United States Patent
Moriya et al.

(12) 
(10) Patent No.: US 6,730,029 B1
(45) Date of Patent: May 4, 2004

(54) ULTRASONIC TRANSMITTER/RECEIVER BY PULSE COMPRESSION

(75) Inventors: Tadashi Moriya, Kanagawa (JP); Norio Tagawa, Tokyo (JP)

(73) Assignee: Japan Science and Technology Corporation, Saitama-ken (JP)

( * ) Notice: Subject to any disclaimer, the term of this patent is extended or adjusted under 35 U.S.C. 154(b) by 0 days.

(21) Appl. No.: 10/088,638
(22) PCT Filed: Sep. 25, 2000
(86) PCT No.: PCT/JP00/06559
§ 371 (c)(1), (2), (4) Date: Jul. 25, 2002
(87) PCT Pub. No.: WO01/21074
PCT Pub. Date: Mar. 29, 2001

(30) Foreign Application Priority Data

Sep. 24, 1999 (JP) .............................. 11-271454

(51) Int. Cl.$^7$ ................................. A61B 8/00
(52) U.S. Cl. ..................................... 600/437
(58) Field of Search ............... 600/407–471; 361/750, 762, 795; 310/344, 353; 606/2, 4, 6, 16, 7, 15, 167; 385/143, 145, 141, 142; 604/20, 22, 35; 73/620–633; 128/916; 367/7, 11, 130, 138

(56) References Cited

U.S. PATENT DOCUMENTS 5,182,790 A * 1/1993 Kayashima et al. ......... 385/141

FOREIGN PATENT DOCUMENTS

| JP | 58-123482 | 7/1983 |
| JP | 59-225375 | 12/1984 |
| JP | UM01-146806 | 10/1989 |
| JP | 02-195952 | 8/1990 |
| JP | 03-143432 | 6/1991 |
| JP | 03-162837 | 7/1991 |
| JP | 05-149963 | 6/1993 |

OTHER PUBLICATIONS

Masasumi Yoshizawa et al., "High signal–to–noise ratio ultrasonic point detection method using a fused quartz rod as pulse compression filter and a sensor", vol. 36. pp. 3157–3159, Japan Journal of Applied Physics (May/1997).

Tadashi Moriya et al., "A simple method for measuring complex acoustic impedance of biological tissues using a fused quartz rod as a transmission line", vol. 2, pp. 1389–1392, IEEE Ultrasonic Symposium (1998).

* cited by examiner

Primary Examiner—Ali M. Imam
(74) Attorney, Agent, or Firm—Radar, Fishman & Grauer PLLC

(57) ABSTRACT

As shown in FIG. 2(a), according to the present invention, a quartz rod is used where, for example, the diameter of the end on the side to which an ultrasound probe attached is 0.58 mm, the diameter at the narrowest portion is 0.3 mm, the diameter at the end on the specimen side is 0.68 mm, and the length is 38 cm. As a result, the diameter on the side of fused quartz rod 20 to which ultrasound transducer 10 allows a favorable range of L (0,3) mode conversion efficiency; and in addition, the diameter of quartz rod 20 on the side coming into contact with specimen 50 is sufficiently large in comparison with wavelength, and in other portions it is set to be sufficiently narrow in order to obtain flexibility. FIG. 2(b) shows a transmission and a reception waveform.

8 Claims, 18 Drawing Sheets

DISPERSION CHARACTERISTICS OF ELASTIC WAVE
PROPAGATING THROUGH A FUSED QUARTZ ROD

CONFIGURATION OF TRANSDUCER AND QUARTZ ROD

SEPARATION OF TRANSMISSION WAVEFORM AND RECEPTION WAVEFORM

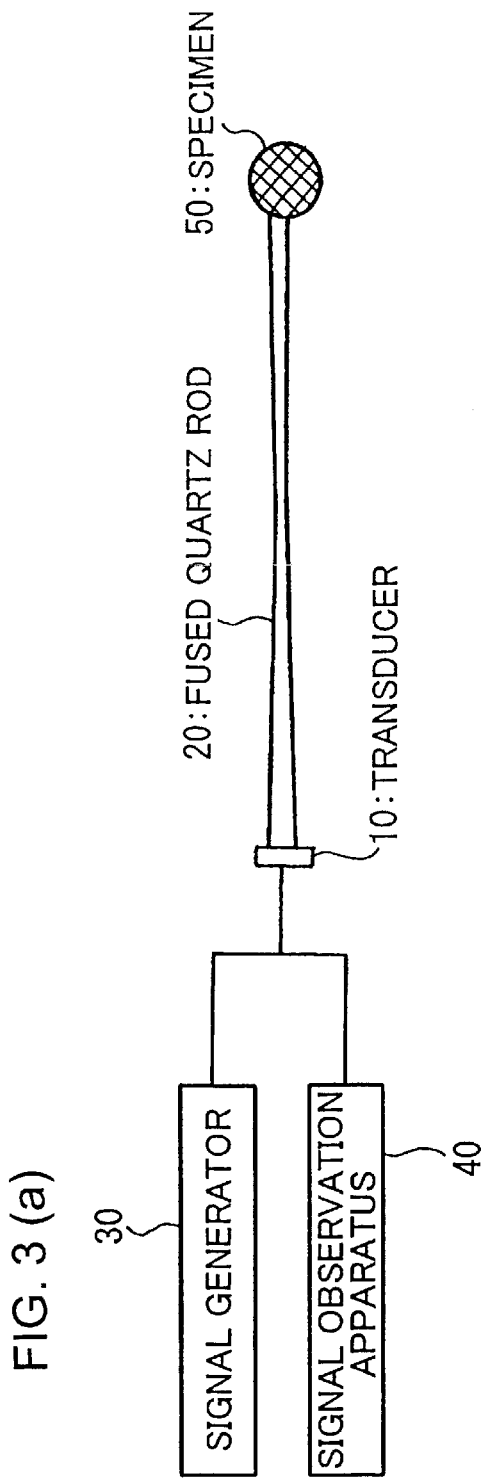
FIG. 3 (a)
FIG. 3 (b)
(1) TRANSMISSION WAVEFORM (NON-LINEAR CHIRP)
(2) RECEPTION WAVEFORM (LINEAR CHIRP)

INTRALUMINAL SYSTEM

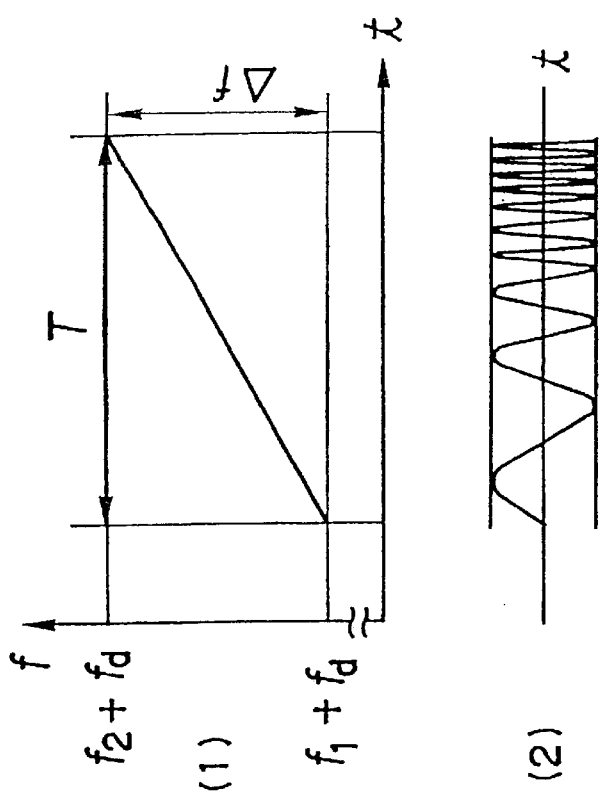
FIG. 8 (a) UP CHIRP WAVE (NO DOPPLER)
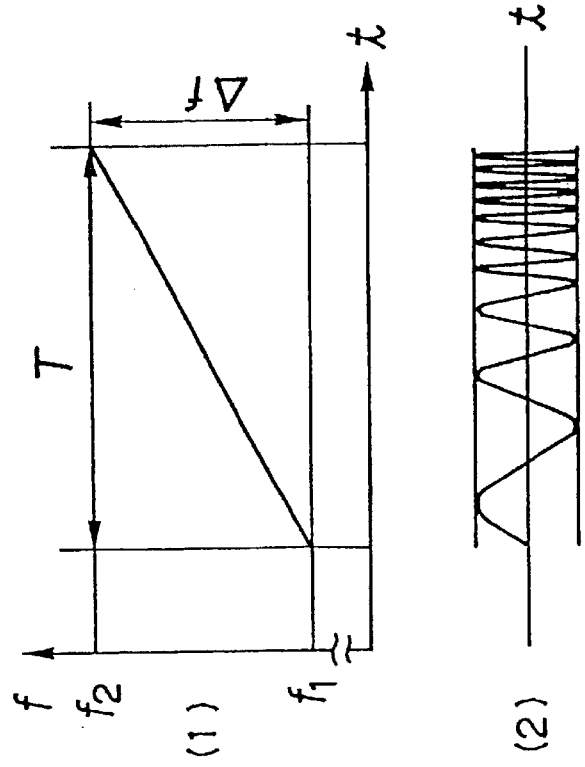
FIG. 8 (b) UP CHIRP WAVE (DOPPLER)

FIG. 9 (a) PULSE COMPRESSION FILTER CHARACTERISTICS (NO DOPPLER)
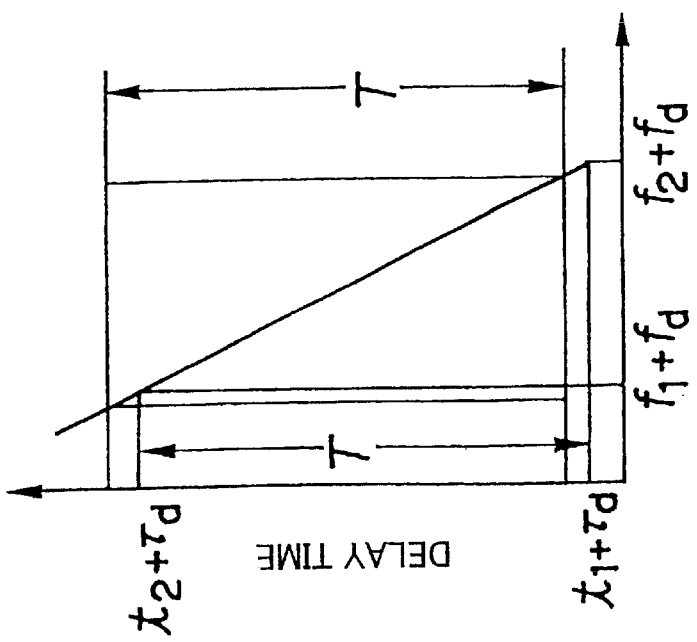
FIG. 9 (b) PULSE COMPRESSION FILTER CHARACTERISTICS (DOPPLER)
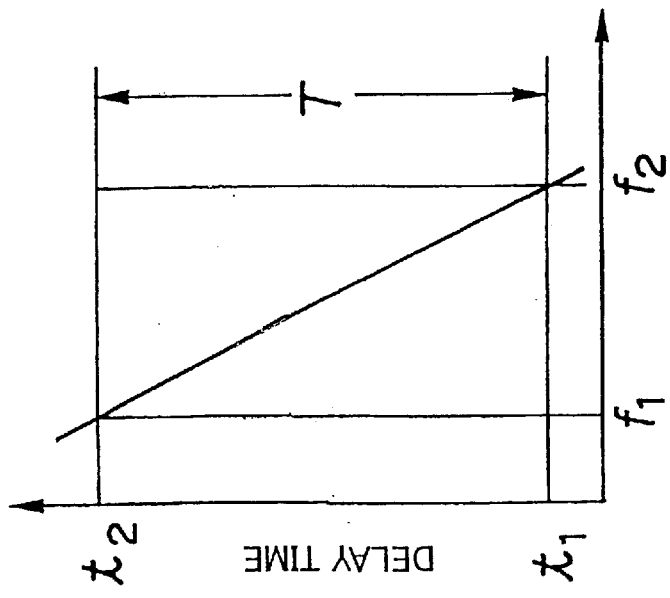

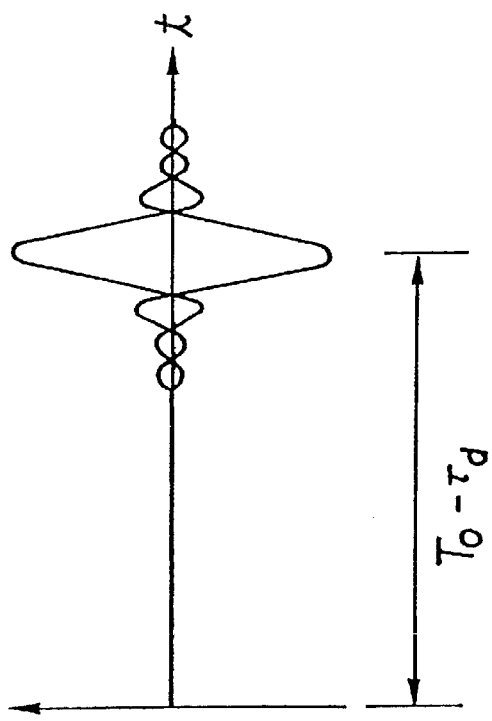
FIG. 10 (a) COMPRESSED WAVEFORM (NO DOPPLER)
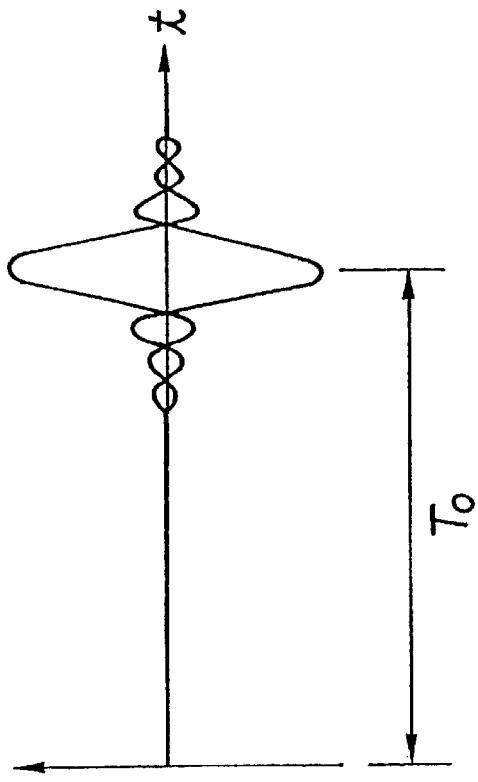
FIG. 10 (b) COMPRESSED WAVEFORM (DOPPLER)

FIG. 11 (a) DOWN CHIRP WAVEFORM (NO DOPPLER)
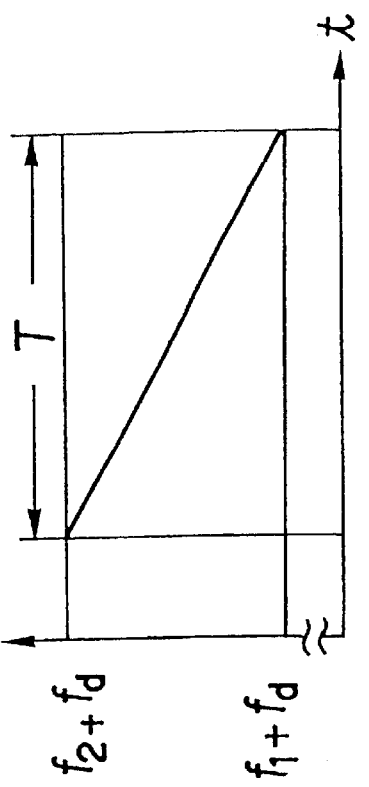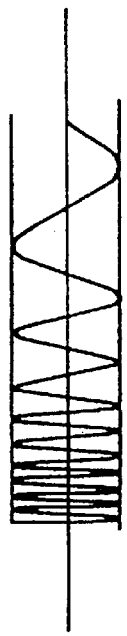
FIG. 11 (b) DOWN CHIRP WAVEFORM (DOPPLER)
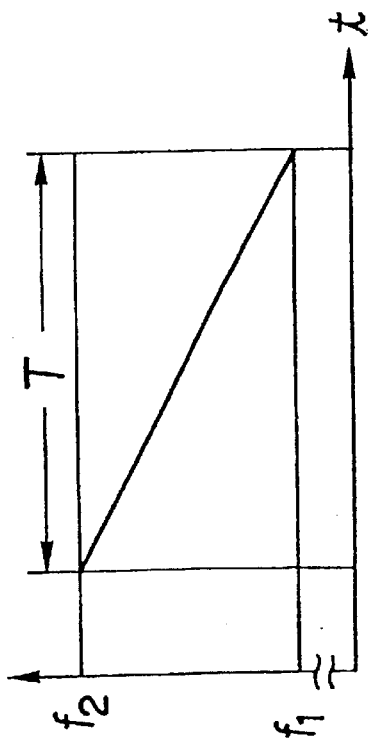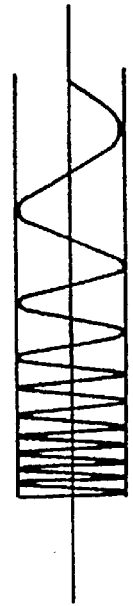

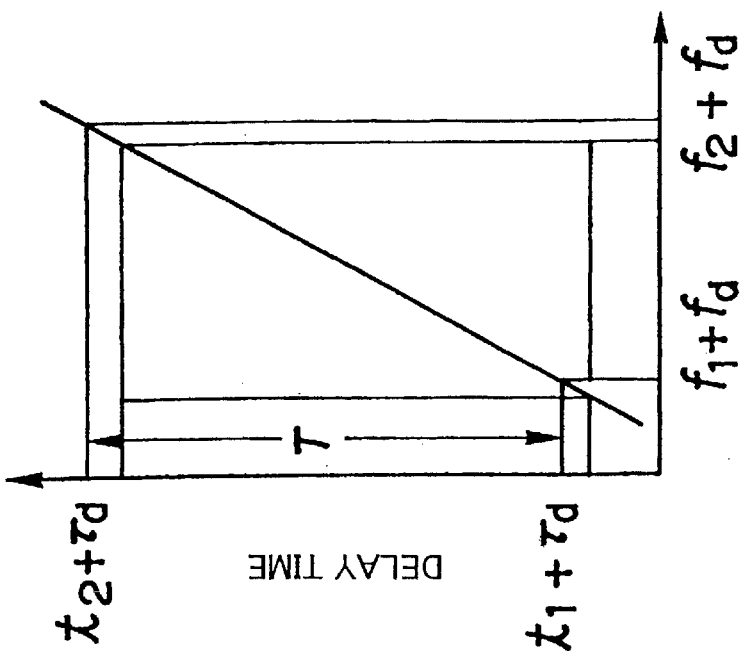
FIG. 12 (b) PULSE COMPRESSION FILTER CHARACTERISTICS (DOPPLER)
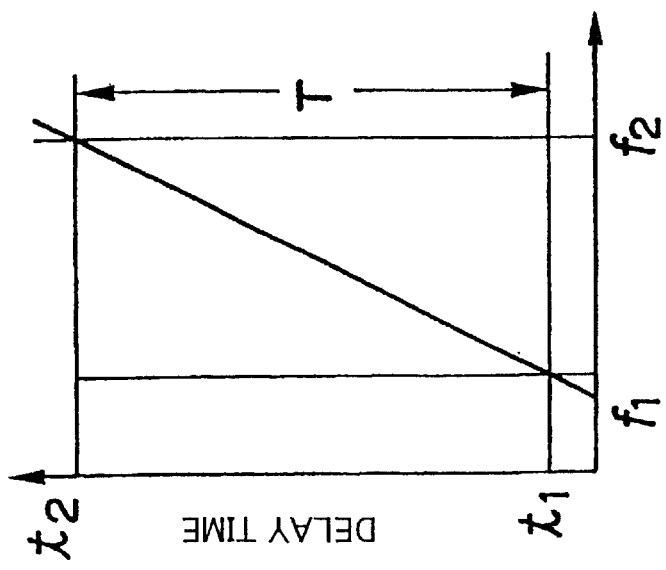
FIG. 12 (a) PULSE COMPRESSION FILTER CHARACTERISTICS (NO DOPPLER)

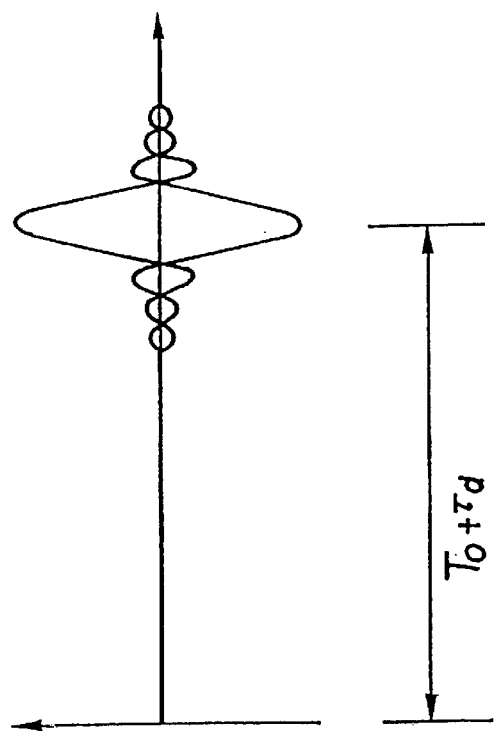
FIG. 13 (a) COMPRESSED WAVEFORM (NO DOPPLER)
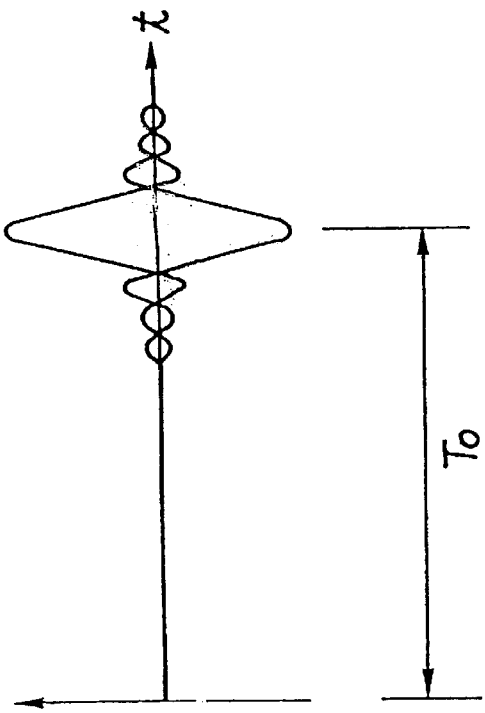
FIG. 13 (b) COMPRESSED WAVEFORM (DOPPLER)

$f_d > 0$ WHEN $f_d = 0$ WHEN $f_d < 0$ WHEN $f_d > 0$ WHEN $f_d = 0$ WHEN $f_d < 0$ WHEN

A: REFLECTION FROM END OF TRANSMISSION LINE

B: REFLECTION FROM ALUMINUM PLATE

5 μs/div

C: REFLECTION FROM ACRYLIC PLATE

5 μs/div

D: REFLECTION FROM OPTICAL FIBER

5 μs/div

ULTRASONIC TRANSMITTER/RECEIVER BY PULSE COMPRESSION

TECHNICAL FIELD

The present invention relates to ultrasound transmission and reception utilizing, for example, ultrasound measurement and imaging in the field of medicine and the field of ultrasound measurement. In particular, it is related to ultrasound transmission and reception using pulse compression.

BACKGROUND ART

Conventionally, measurement has been performed and images obtained utilizing reflected ultrasound waves and the like. For example, with an ultrasound diagnosis apparatus, a tomogram of an organism is obtained by transmitting an impulse wave from an ultrasonic transducer, receiving back the reflected echo, and then being subjected to image processing. For such an ultrasound diagnosis apparatus, the deepest invasion depth and highest resolution possible is required.

There is a pulse compression technique that satisfies this requirement. With this, an originally long pulse is shortened and compressed by subjecting an ultrasonic signal that is to be transmitted to FM modulation (hereafter the resulting signal is referred to as a chirp signal) and upon reception, passing it through a filter corresponding to the chirp signal. An attempt is made to increase resolution due to the compression, and at the same time improve the signal-to-noise ratio, and improve the invasion depth.

With such pulse compression, since the transmitted signal and the received signal are temporally separate, it is necessary to separate the transducer from measurement subject. The region in between is called the separation region. For example, with an ultrasound microscope, the separation region is configured by a line that has a sufficiently large diameter in comparison to the signal wavelength and that is used as a delay medium. This line cannot be regarded as a waveguide because it may not be flexible due to the fact that it is allowed to have an infinitely large diameter. Here the waveguide is said to have no change in amplitude distribution within cross sections within the entire propagated distance. In this case, transmission/reception of a pulse having a long duration of 100 $\mu$s or longer using the 20 Mhz band is practically difficult. In addition, since this line has no flexibility, it cannot be adapted for ultrasound endoscopes, etc. As a method in place of this, there is a method that uses separate probes for transmission and reception. In addition, a circulator is used with a 25 Mhz or higher band. However, a reflection occurring due to mismatch between the transducer and the transmission medium is additionally mixed into the reception system.

Pulse compression is widely used with the objective of attempting to increase transmission energy under the limitation of transmission peak-power in the field of radar and sonar in order to increase survey distance and/or gain higher resolution. Much research on introducing the pulse compression technique with similar objectives is also being carried out in the field of medical ultrasound. Notwithstanding benefits such as being able to improve resolution in a predetermined region in order to allow manipulation of the transmission signal spectrum in the time domain, this pulse compression technique has yet to reach realization in the field of medical ultrasound.

The biggest hurdle to bringing this into use is the need for a separation region, and the next hurdle is suppression of the side lobes after pulse compression. The problem with the latter is that due to the signal of a small reflective body becoming buried by the side lobes of a signal from a large reflective body.

Speaking of the separation region problem, with the pulse compression technique, the long pulse width of the transmitted pulse signal, which is hundreds of micro seconds long, causes separation to become great. A soft plastic board is ordinarily used to provide this region. In actuality, this method is very difficult to deal with. In addition, this method is not applicable to ultrasound endoscopes, etc. Another way of avoiding this method is using separate proves for transmission and reception. However when separate probes for transmission and reception are used, only a signal from the region where the transmitted ultrasound beam intersects the region where the reception transducer can receive, and the obtained image is poor. Furthermore, for reception of a mixed transmission signal and reception signal it is not practiceal because it requires an amplifier with extremely large dynamic range. Accordingly, a method of separating a transmission signal and a reception signal with an integrated transmission/reception probe is desirable.

DISCLOSURE OF THE INVENTION

The object of the present invention is to solve the following problems occurring in conventional ultrasound transmission and reception.

1. In pulse compression, a transmission signal and a reception signal having long duration cannot be temporally separated by a single transducer.
2. After compression, side lobe level suppression is insufficient.

Once these methods are developed, various applications such as detection of an extremely weak signal and Doppler measurement will become possible.

In order to achieve the above-mentioned object, an ultrasound transmission/reception apparatus, which performs pulse compression on a received ultrasound signal using a signal with temporally changing frequency as an ultrasound signal to be transmitted, is characterized by a transducer common for receiving and transmitting said ultrasound signal and a transmission line common for propagating said ultrasound signal, wherein a flexible waveguide transmission line is used as said transmission path, and said transmission line is used as a delay medium to temporally separate a received ultrasound signal and a transmitted ultrasound signal with long duration. A quartz rod where the center portion is made narrow can be used as this transmission line.

For said ultrasound signal to be transmitted, a signal where frequency changes but not dependent on time may be used. In this case, said signal to be transmitted may be a signal that becomes a signal where frequency changes in proportion to time when received. When the transmission line is long, a chirp signal with a changing frequency becomes distorted; however, by using a non-linear chirp signal where frequency changes but not in proportion to time, it becomes possible to reduce the distortion in the received signal.

Side lobe suppression can be performed after pulse compression of a received ultrasound signal, by taking the correlation with an ideal compression waveform during further compression.

By coding a plurality of ultrasound signals delayed a certain length of time in conformity with whether or not being sent according to a code series, and transmitting them, and after pulse compressing the received signals, they may be decoded in conformity with the code series that has been coded. In this manner, by transmitting a plurality of signals in accordance with the code series, two-step compression processing becomes possible, and a reception signal with an even higher SIN ratio can be obtained.

By using an up chirp signal and a down chirp signal as the ultrasound signal to be transmitted, and performing analysis of the time difference or spectrum of, for example, the compressed pulses obtained through processing said respective signals received, it is possible to accurately measure the Doppler effect.

In addition, the above mentioned transmission/reception configuration can be applied to configure an interluminary system.

BRIEF DESCRIPTION OF DRAWINGS

FIG. 3 is a diagram describing use of a non-linear chirp signal.

FIG. 8 is a diagram describing the Doppler effect on an up chirp signal.

FIG. 9 is a diagram describing the pulse compression processing of an up chirp signal.

FIG. 10 is a diagram describing the result of pulse compression processing.

FIG. 11 is a diagram describing the Doppler effect on a down chirp signal.

FIG. 12 is a diagram describing the pulse compression processing on a down chirp signal.

FIG. 13 is a diagram describing the result of pulse compression processing.

BEST MODE FOR CARRYING OUT THE INVENTION

The best mode for carrying out the invention is described in detail forthwith while referencing the drawings.

Temporal Separation of Transmission Signal and Reception Signal

To begin with, temporal separation of a transmission signal and a reception signal is described.

In the present invention, the separation region for performing temporal separation is configured using a flexible waveguide transmission line.

Figure 1:
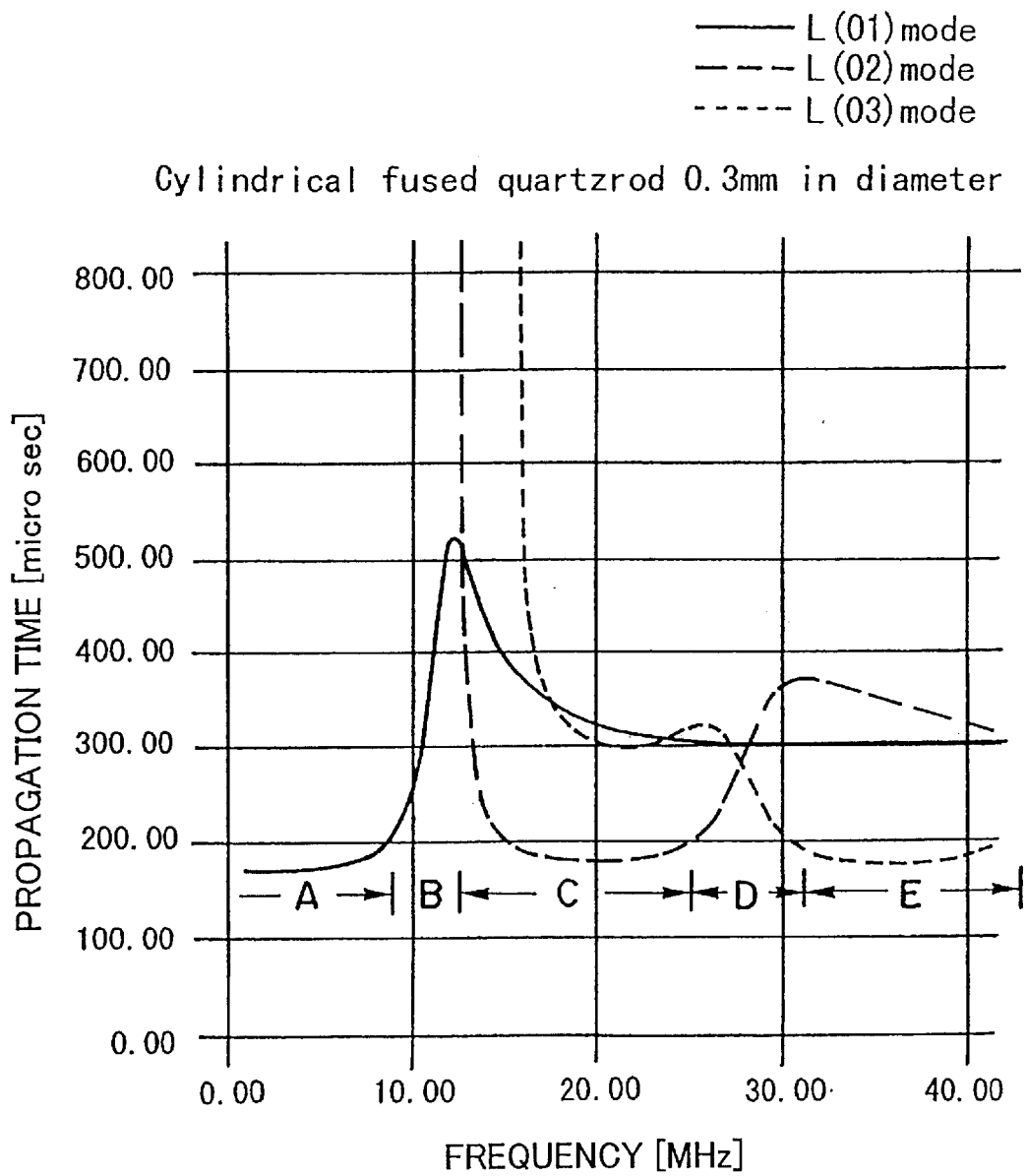
FIG. 1 is a graph showing dispersion characteristics of elastic waves transmitted through a fused quartz rod.

As shown in FIG. 1, the propagation features of the L (0,1) mode, the L (0,2) mode, and the L (0,3) mode of an elastic wave propagated through fused quartz rod are clearly shown (refer to IEICE Trans. Commun., Vol. J69-A, No. 8, pp. 1006–1014, 1986 and IEICE Trans. Commun., Vol. 109-C, No. 8, 1989, pp. 581–586). It is noted that, L (0,1) mode, L (0,2) mode, and L (0,3) mode correspond to waves that, among the elastic waves transmitted through a cylindrical elastic rod, are longitudinal waves and do not change towards the circumference. These are referred to as L (0,1) mode, L (0,2) mode, and L (0,3) mode, in order from the simplest mode, and are distinguishable because propagation time differs for each.

Nevertheless, since the objective has been to form a pulse compression filter using a region (region B and region D in FIG. 1) having large dispersion (or the difference in propagation time due to frequency), transmitting a chirp signal through a region having small dispersion was not considered. It is understood that there is small dispersion and a high conversion efficiency from an electric signal to an ultrasound signal in regions A, C and E (refer to Japanese Journal of Applied Physics, Vol. 27, Supplement 27-1, pp.117–119, 1988). In the present invention, transmission of a signal where the frequency thereof climbs over time (up chirp signal) or a signal where the frequency thereof decreases over time (down chirp signal) through a fused quartz rod using as wide a range as possible is considered.

Here, a method for configuring a flexible transmission line using the region E of L (0,3) mode of a quartz rod is discussed. To begin with, in order to oscillate ultrasonic waves having a frequency of 20 MHz using the E region of L (0,3) mode, it is necessary to use quartz rod with a diameter of approximately 0.5 mm. Moreover, in order to transmit plane waves without expanding the ultrasound beam within a specimen that is to be measured (preferably, the ultrasound wave converging within the specimen), a transmission line having a sufficiently wide cross-sectional area compared to wavelength (since wavelength of an ultrasound wave within an organism at 20 Mhz is approximately 75 $\mu$m, a circular end surface with a diameter of approximately 0.75 mm, which is ten times larger) must be used. On the other hand, in order to preserve flexibility, a transmission line that is as thin as possible must be used. Accordingly, with the present invention, a taper-shaped quartz rod, which is thick at both ends and gradually becomes thin at the center is used.

Taper-shaped Quartz Rod

Figure 2:
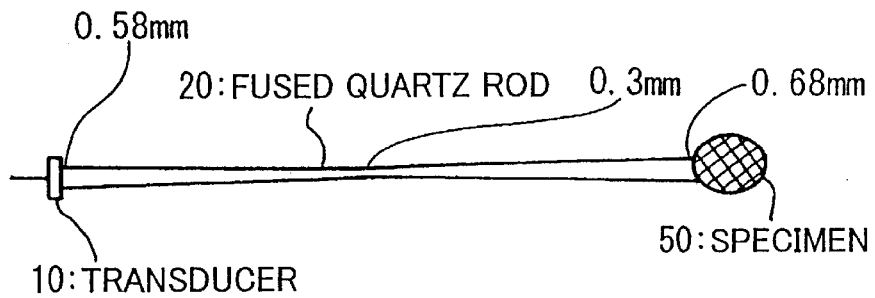
FIG. 2 is a diagram for describing separation of a transmission signal and a reception signal using a quartz rod.
Figure 2:
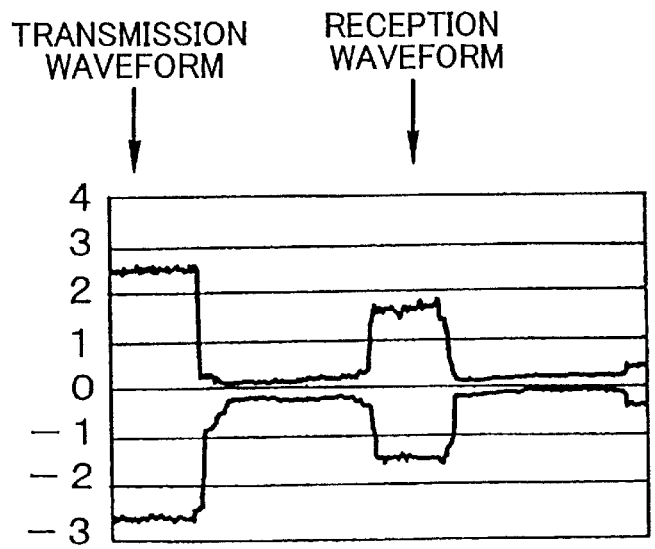

In the case of using a taper-shaped quartz rod, since portion of the C region and the D region are used, testing must be performed to find approximately to what ratio of end surface and center portion is allowed. As shown in FIG. 2($a$), with the present invention, results of actual testing on each type of taper-shaped quartz rod require the use of fused quartz rod 20 with the diameter of the side connected to an ultrasound probe being approximately 0.58 mm, the diameter of the smallest portion being 0.3 mm, the diameter of the end face being 0.68 mm, and the length of the rod being 38 mm. This shows that the diameter of the side of fused quartz rod 20 to which ultrasound transducer 10 is attached is set so as to fall within a favorable range of conversion efficiency in L (0,3) mode; in addition, the diameter of quartz rod 20 on the side which comes into contact with specimen 50 is set large enough compared to wavelength, and the rest of the portions are set thin enough to preserve flexibility.

In this case, it is confirmed that ultrasound waves can be transmitted at between 18 Mhz and 21 Mhz with little waveform distortion and under little influence from other modes. The transmission waveform and the reception waveform are shown in FIG. 2(b). In addition, favorable operation between 29 Mhz and 33 Mhz is also confirmed.

Non-linear Chirp Signal

Since there is dispersion even in the region described above within quartz rod 20, when the distance needed to form the separation region becomes approximately 1 meter, the waveform becomes distorted. Thus, compensation becomes necessary. In the present invention, the fact that the waveform of the chirp signal is easily controlled in time-domain is utilized, and configuration is made so that the transmission chirp signal is made a non-linear chirp signal (a signal for which frequency does not vary in proportion to time], and its characteristics are configured so that the waveform after reception can be a linear chirp signal (a signal for which frequency varies in proportion to time]. This is described with FIG. 3.

In FIG. 3(a), the signal generated by signal generator 30 is made a non-linear chirp signal as described above, and this non-linear chirp signal is applied to fused quartz rod 20 from transducer 10 as a transmission signal. The non-linear chirp signal propagates through fused quartz rod 20, is reflected at the specimen 50, propagates again through the same fused quartz rod 20, and is received by transducer 10. This reception signal is a linear chirp signal. The waveform of the transmission signal as a non-linear chirp signal, and the reception signal as a linear chirp signal are shown with FIG. 3(b) (1) and (2), respectively. How to find the transmission signal as a non-linear chirp signal is described in detail later.

This makes it possible to transmit both an up chirp signal and down chirp signal through the same transmission line, and makes it easy to perform signal processing such as removing the effect of frequency dependence decay within an organism or Doppler signal detection. It is noted that since L (0,3) mode propagation time, as can be seen in FIG. 1, is approximately 100 $\mu$s per meter, it is necessary to adjust the length of the propagation line in conformity with the pulse width of the transmitted signal.

How to Find the Non-linear Chirp Signal

As an example of how to find the non-linear signal, the E region in the L (0,3) mode of an elastic wave [Pochhammer-Chree waves] propagating through the fused quartz rod is used; one end of the fused quartz rod is attached to the transducer; the other end is used as a coupler to a subject to be observed; a non-linear frequency modulated signal, which compensates dispersion in the elastic wave, is used as a transmission signal; and the reception signal is made a linear chirp signal.

In this case, let H ($\omega$) be the transfer function for the transmission line, and C ($\omega$) be the Fourier transform of the linear chirp signal; the transmission non-linear chirp signal can be found from the reverse Fourier transform of C ($\omega$)/(H ($\omega$)+$\kappa$). Here, $\kappa$ is determined using a criterion such as the minimal square error between the ideal chirp signal and the planned chirp signal.

Side Lobe Suppression

Figure 4:
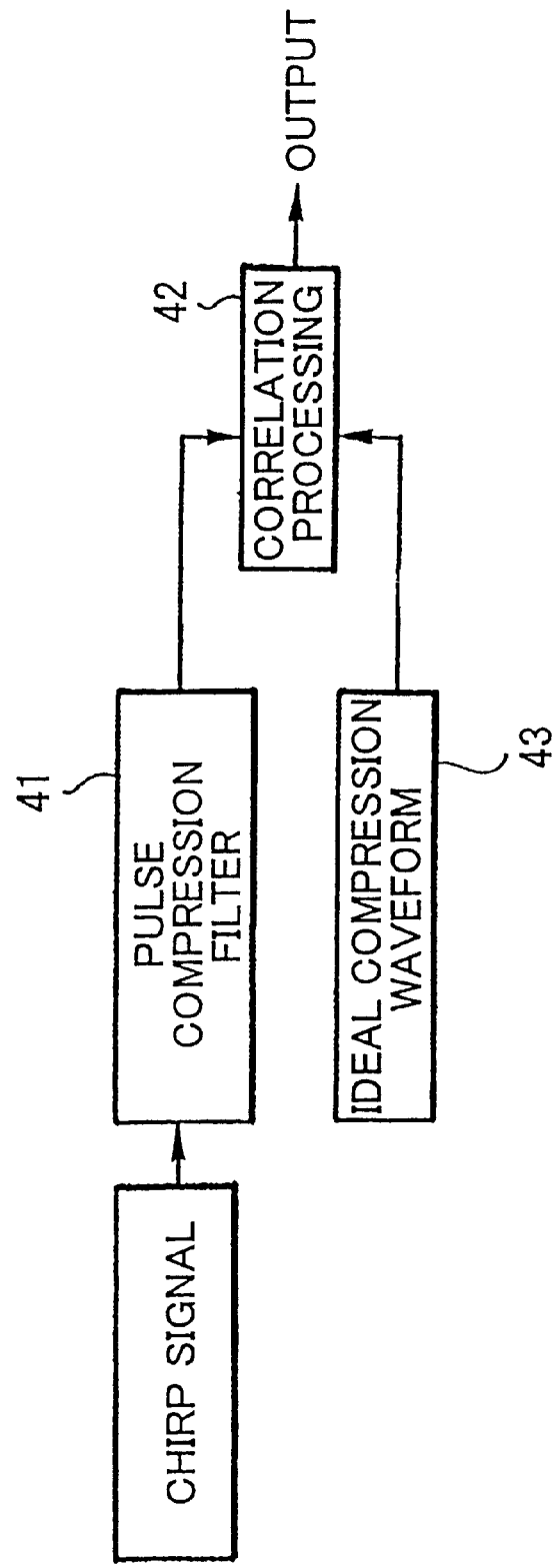
FIG. 4 is a diagram for describing side lobe suppression.

For example, in a medical ultrasound imaging apparatus, it is necessary to detect a small reflective body that is near a large reflective body. As a result, side lobe suppression of the reflective wave is the biggest problem in pulse compression attempting to increase resolution. In order to suppress side lobes with the present invention, as shown in FIG. 4, the waveform of the received chirp signal from the specimen is compressed by pulse compression filter 41, and is then correlated to the ideal compressed waveform, which is of pulse compression filter 41 and which is output from waveform generator 43. By calculating a cross-correlation, since the output of the cross correlation between two similar waves is high when they match, this can be used to suppress side lobes.

Figure 5:
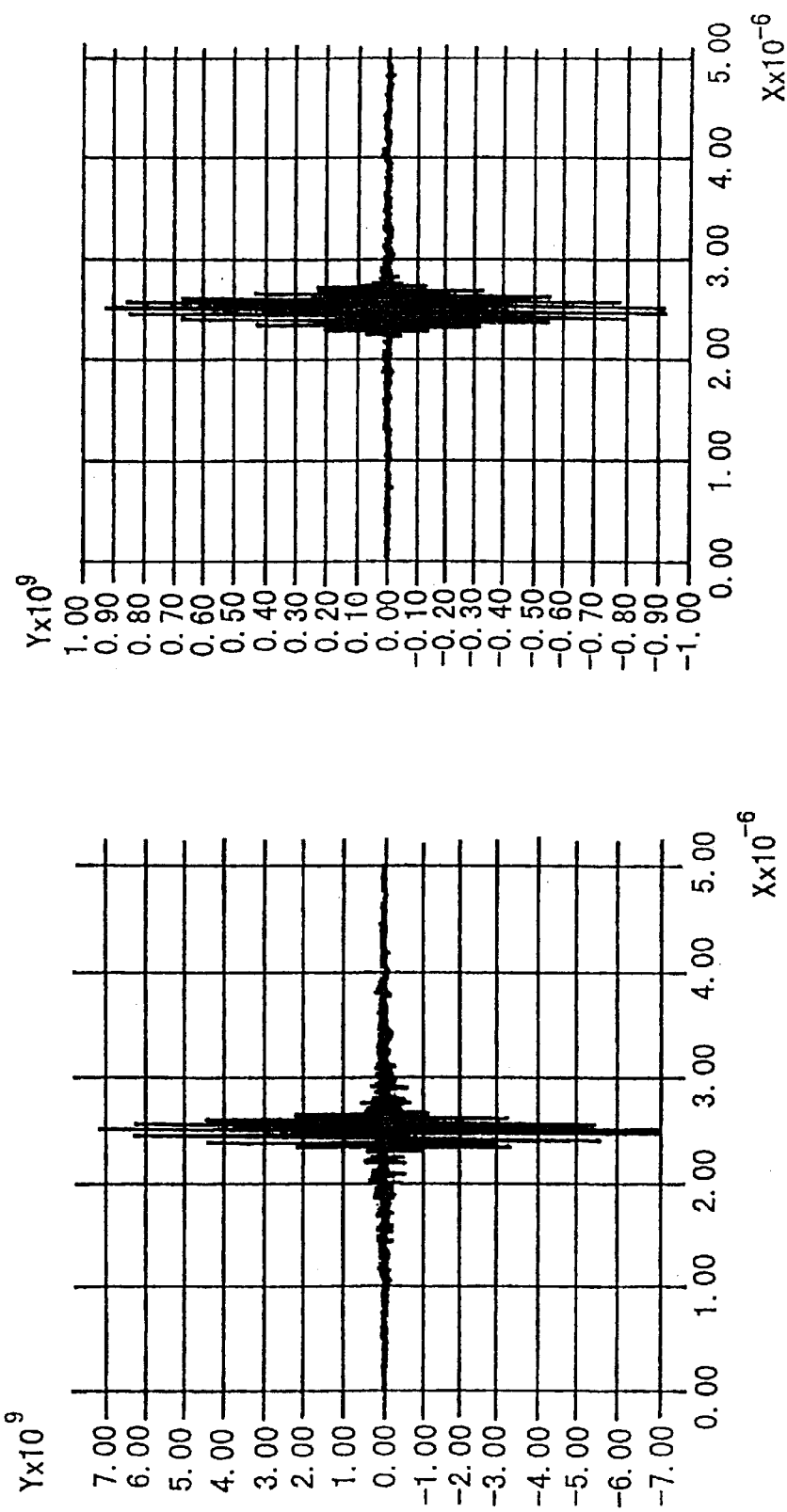
FIG. 5 is a diagram describing simulation of side lobe suppression.

FIG. 5(a) is a waveform diagram of the output of the received chirp signal from pulse suppression filter 41; and FIG. 5(b) is a waveform chart of the output from correlation processing unit 42. From these waveform charts, it is clear that the side lobes are suppressed.

Two-step Compression Method

This method can be made applicable for an encoding method using an M-series (a time series of random pulses) by adjusting so that a non-linear chirp signal corresponding to an M-series is transmitted and received and pulse compressed to obtain a match for the M-series. According to this method, separation of the reception signal from the transmission signal and multiplexing of M-series is possible. In addition, since the overall compression ratio with this method is the product of the compression ratio of the chirp signal and the compression ratio of the M-series, a large compression ratio can be obtained.

Figure 6:
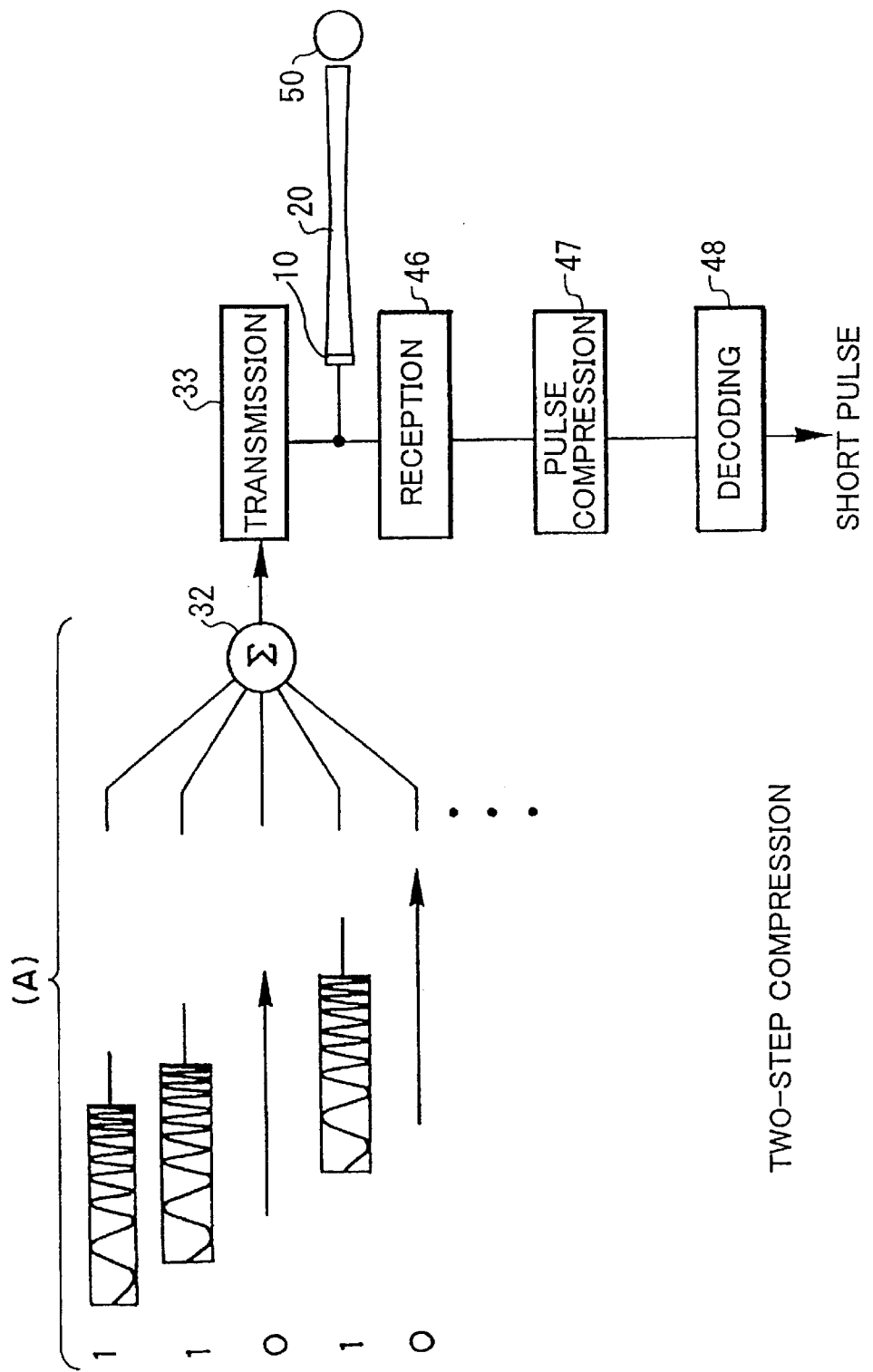
FIG. 6 is a diagram describing two-step pulse compression.

This is described in more detail using FIG. 6. Generation of a signal is shown in section A of FIG. 6. In other words, a plurality of chirp signals, each delayed a certain fixed length of time, are generated, and in response to a M-series of codes, for example 1, 1, 0, . . . , the temporally delayed chirp signals are sent out, respectitively. A chirp signal is sent out when the M-series is "1", and no signal is sent out when "0"; then after this plurality of signals conforming to the M-series are combined through synthesizer 32, they are transmitted from transmitter 33. After receptor 46 receives the signal from the specimen, compression of the chirp signal is first performed by pulse compression filter 47, and a pulse string corresponding to the M-series is generated. Next, a signal matching the same M-series at the time of transmission is decoded by decoder 48, obtaining a single short pulse. In this manner, since compression with a two-step compression comprising compression in conformity with the chirp signal and compression in conformity with the M-series is carried out, observation with a high signal-to-noise ratio is possible.

It is noted that it is possible to apply the above-mentioned side lobe suppression to this two-step compression processing, and perform side lobe suppression after processing by the pulse compression filter.

This two-step pulse compression can also be applied to radar, sonar, and spread-spectrum communication.

Intraluminal Ultrasound Endoscope System

Figure 7:
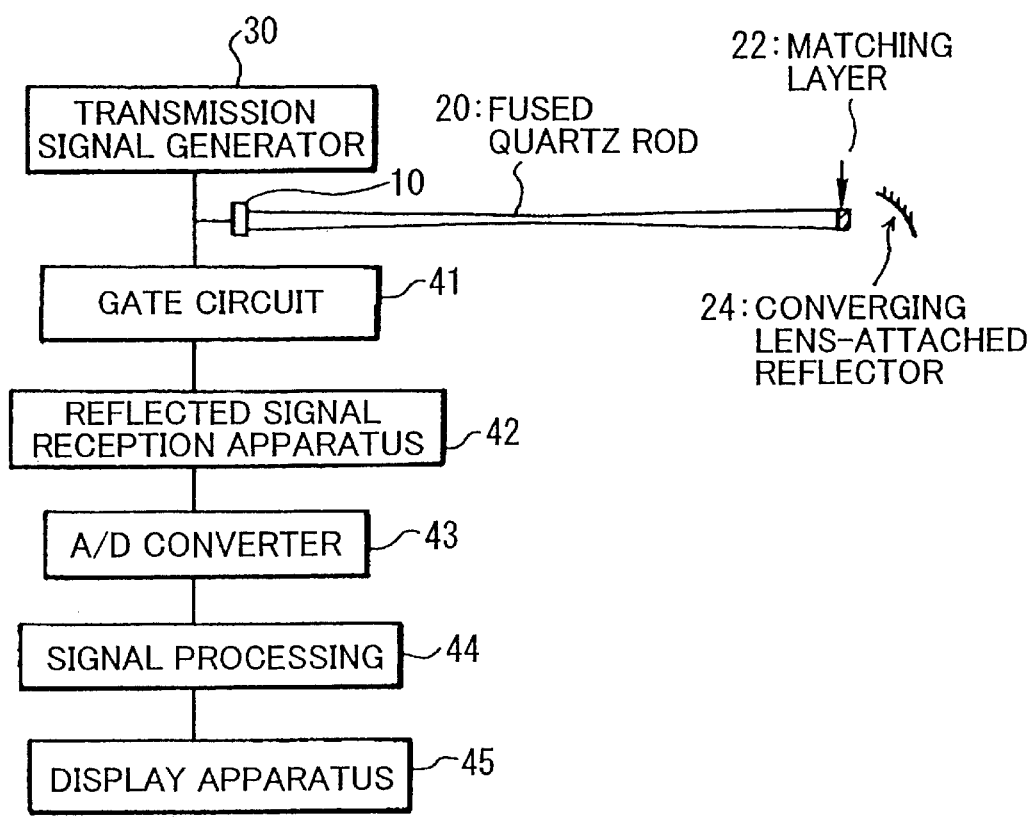
FIG. 7 is a diagram describing configuration of an intraluminal system.

An example of applying the present invention to an intraluminal ultrasound endoscope is described forthwith using FIG. 7. An ultrasound endoscope of a system where the object to be viewed is a lumen such as inside a blood vessel or inside the uterer, and where a probe mechanically rotates, is used with ultrasound transducer 10 built into the catheter. It is easy to introduce pulse compression to this system by using a method of separating the transmitted signal and the reception signal according to the present invention.

This is shown in FIG. 7. More specifically, since an L (0,3) mode elastic wave in the 20 Mhz band propagates through a quartz rod having a diameter between approximately 0.3 mm and approximately 0.7 mm, it is possible to insert the quartz rod into a hollow metal line by employing appropriate protection such as winding with silk thread. Since quartz rod 20 having such thickness is flexible, it can be used inserted into a catheter. The diameter of the coupler portion is set to accommodate the measurement depth by using a taper-shaped quartz rod. Moreover, the acoustically matching portion (matching layer) 22, the refractive surface, and lens (in this example, focusing lens-attached reflector 24) for acoustic beam are positioned. This lens can be set near the specimen to be observed. The ultrasound wave excited through ultrasonic transducer 10 irradiates the subject region through fused quartz rod 20 and the coupler, and the reflected signal propagates back through quartz rod 20 and is converted to an electric signal again by transducer 10. By setting the transmission signal so the received signal can be a linear chirp signal, the received signal is converted to a compressed pulse through standardized signal processing using signal processing unit 44 after passing through a standardized pulse compression filter or A/D converter. This can be observed with display unit 45.

With this system it is possible to use a non-linear chirp signal as the transmission signal and perform side lobe suppression using an ideal output waveform of the above-mentioned pulse compression filter as the reception signal processing.

In addition, it is possible to use the above-mentioned two-step pulse compression processing.

Doppler Signal Measurement

When linear chirp signal is applied a Doppler shift, it is known that the spectrum is frequency shifted without having less change in the shape of compressed signal waveform. Here, it is described that the up chirp signal and the down chirp signal are transmitted simultaneously through the transmission line described above, that the fact that spectrum of the signals reflected from the same region shift opposite directions is used, and that the detection of the Doppler signal is done by comparing these spectrums. It is possible to detect motion velocity within a wide region by changing the rate of frequency change in the transmission chirp signal.

To begin with, Doppler shift of an up chirp signal and a down chirp signal is described in detail using FIG. 8 through FIG. 13.

FIG. 8 through FIG. 10 describe temporal shift of a waveform after compression depending on whether the Doppler effect is present in the case of an up chirp signal.

A case where there is no Doppler effect is first considered. FIG. 8($a$) schematically shows a linear frequency modulated chirp signal, which is a chirp signal of pulse width T and the frequency of which showing a linear increase from $f_1$ to $f_2$ =$f_1$+$\Delta t$. This waveform is input to the pulse compression filter, which has the characteristics of FIG. 9($a$). In this filter, the low frequency band yields greater time delay and as frequency becomes higher, time delay decreases linearly. It is to be assumed that where the frequency is f1, the time delay is t2, and where the frequency is f2, the time delay is t1=t2−T. Once the up chirp signal is input to this filter, the signal input earlier in time progresses slowly, whereas a high signal moves more quickly, thus the chirp signal after passing through the filer, is compressed creating a waveform such as that shown in FIG. 10($a$). At this point, time delay from an arbitrary standard time is assumed to be $T_0$.

Next, a case where there is Doppler effect is considered. It is to be assumed that the chirp signal shown in FIG. 8($a$) is applied a frequency shift (Doppler shift) in conformity with the Doppler effect shown in FIG. 8($b$) to become a chirp signal that has changed from $f_1$+$f_d$ to $f_2$+$f_d$. Here $f_d$ denotes the Doppler frequency representing the frequency shift of the Doppler effect, and is assumed to be positive. The case where the chirp signal applied this frequency shift is input to a pulse compression filter with the same features as shown in FIG. 9($a$) is shown in FIG. 9($b$). As shown in this figure, the time delay corresponding to frequency $f_1$+$f_d$ is small with $t_2$−$\square_d$. Here, $\square_d$=T·$f_d$/$\Delta f$. Accordingly, the delay of the compressed waveform also is small, and after passing through the filter, the chirp signal takes on a waveform such as shown in FIG. 10($b$), and the delay from the reference time is $T_0$−$\square_d$.

Next, the case of a down chirp signal is considered. FIG. 11 through FIG. 13 describe the misalignment of the waveform after compression in conformity with whether the Doppler effect is present, in the case of an up chirp signal.

First, the case without the Doppler effect is considered. FIG. 11($a$) shows a chirp signal whose frequency shows linear reduction from $f_2$ to $f_1$=$f_1$−$\Delta f$. When this signal is input to the pulse compression filter with the features shown in FIG. 12($a$), given that in this filter, time delay is greater for $f_2$, and time delay is smaller for $f_1$=$f_1$−$\Delta f$, since the high frequency components input to the filter first proceed slowly, and the low frequency components input later proceed faster, a compressed waveform such as the one shown in FIG. 10($a$) is obtained. Here, time delay from the standard time is set as $T_0$.

Next, the case with the Doppler effect is considered. It is assumed that the chirp signal shown in FIG. 11($a$), after being affected by the frequency shift of the Doppler effect, has become the chirp signal which shift from $f_2$+$\square_d$ to $f_1$+$\square_d$=$f_2$−$f_1$+$\Delta f$. When these signal is input to a pulse compression filter with the same features as shown in FIG. 12($a$), since frequencies as a whole have been on the rise, time delay of the compressed waveform from the standard time becomes $T_0$+$\square_d$.

As shown in FIG. 10 and FIG. 12, after being compressed, since the signals of the up chirp signals and the down chirp signals respectively shift in opposite directions due to the Doppler effect, detection of this shift makes it possible to detect the Doppler signal itself.

Next, how to determine if the Doppler effect is detected is described. Let the Fourier transform of the compressed waveform of the up chirp signal shown in FIG. 10($a$) be $F_U(\omega)$. With the signal having the Doppler effect shown in FIG. 10($b$), since the signal temporally shifts $\square_d$ without any change in waveform, the Fourier transform of this waveform becomes $F_U(\omega)e^{j\omega\square_d}$. Similarly, if it is assumed that the Fourier transform of the waveform of the down chirp signal in FIG. 13($a$) is $F_D(\omega)$, the Fourier transform of the waveform of the signal with the Doppler effect shown in FIG. 13($b$) becomes $F_D(\omega)e^{j\omega\square_d}$.

Accordingly, in the case where there is no Doppler effect, for example, if the system is adjusted so as to have $F_U(\omega)$= $F_D(\omega)$, from the measurement values of $F_U(\omega)e^{j\omega\square_d}$ and $F_D(\omega)e^{j\omega\square_d}$, it is possible to obtain $\square_d$=T·$f_d$·$\Delta f$, or in other words the Doppler frequency $f_d$.

It is noted that, in this description, the case where the Doppler signal increases is considered; however, in the case where the signal decreases, the principle remains the same only the direction of the shift takes place in the opposite direction.

Figure 14:
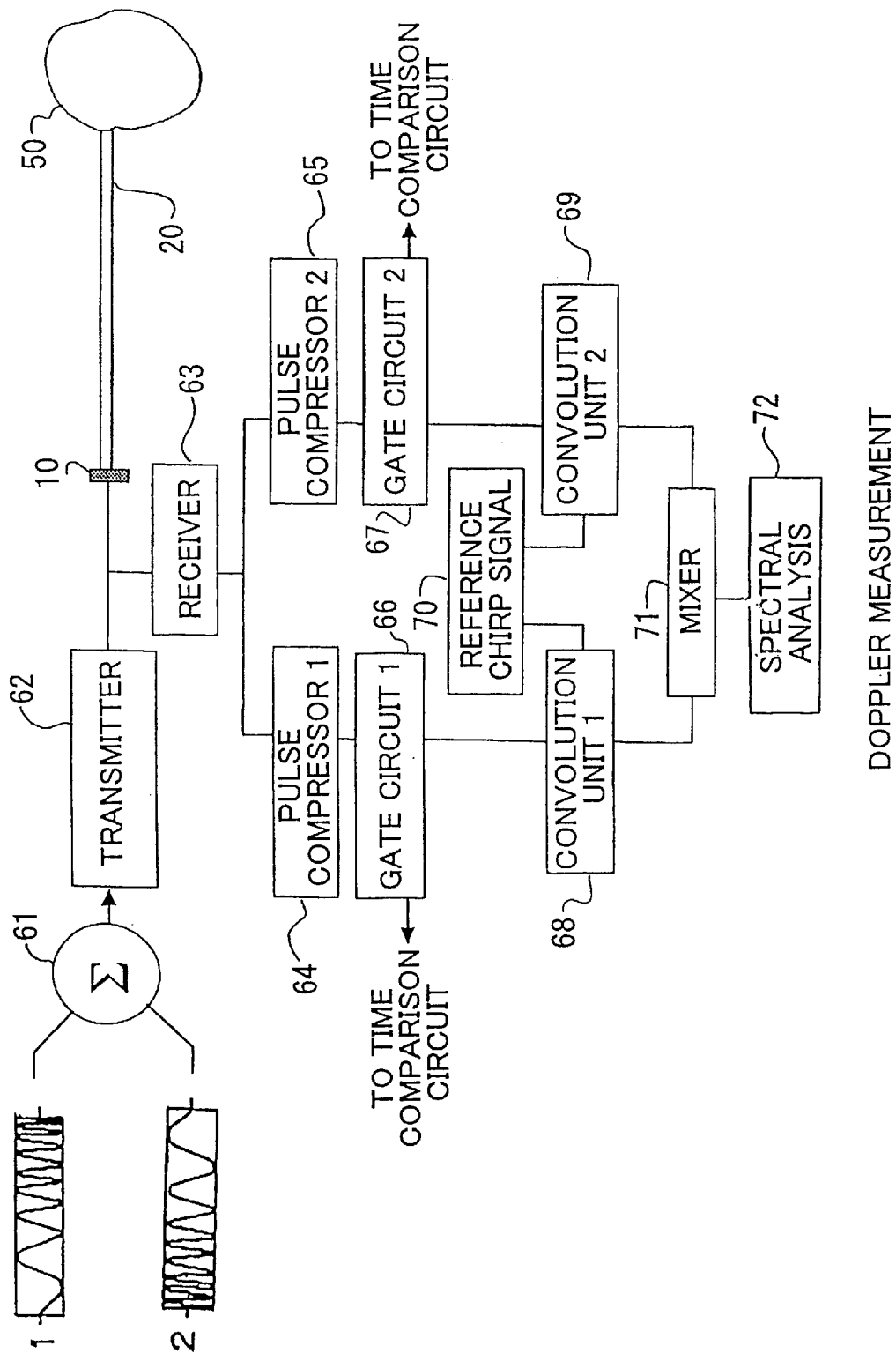
FIG. 14 is a diagram describing measurement of the Doppler effect.

An apparatus, which applies this principle to detect the Doppler frequency, is shown in FIG. 14.

In FIG. 14, up chirp signal 1 and down chirp signal 2 are synthesized at synthesizer 6 and then transmitted. As for the signals transmitted to the specimen through a transmission line according to the present invention, signal 1, after being received, is compressed by up chirp signal pulse compression system 64, and at gate circuit 1 66, the signal of the target location is picked up. Down chirp signal 2 is also compressed by down chirp pulse compression system 65, and at gate circuit 2 67, the signal of the target location described earlier is picked up.

In the case where Doppler measurement is performed together with compressed pulse target location detection, the signal of the respective target locations from gate circuit 1 66 and gate circuit 2 67 is transmitted to the time comparison circuit (not shown in the drawings). Using the time comparison circuit, measurement of the Doppler effect at the respective target locations is performed using the time difference of up chirp signal 1 and down chirp signal 2, respectively. This is described in detail later.

In the case of spectral Doppler frequency detection, the pulse that is the output of the gate circuit 1 66, and the pulse that is the output of the gate circuit 2 67 are respectively convoluted at convolution unit 1 68 and convolution unit 2 69 with the standard chirp signal (up chirp signal 1 or down chirp signal 2) from the standard chirp signal generator. As a result, since chirp signals having a time difference are obtained, spectrum analysis is performed after these signals are input to mixer 71 and multiplied. Picking up lower frequency components, the beat of two chirp signals having a time difference is obtained. Thus, the Doppler frequency at the target position can be obtained. It is noted that by matching the characteristics of the gate circuit 1 66 and the gate circuit 2 67, the influence from the window function can be reduced to a minimum.

This spectrum analysis will be described in detail later.

Transmission of a signal for measuring the Doppler effect can be performed using the quartz rod shown in FIG. 2; however, the present invention is not limited to this.

Transmission and reception of these signals can use the non-linear chirp signal described above, and for suppression of side lobes, side lobe suppression processing using deal output waveforms of the pulse compression described above can also be performed.

When this method is applied, for example, to detect the velocity of blood flow in an organism, additional use of a low-density ultrasound contrast agent (tracer) can assure a more accurate detection of blood. In addition, since blood flow observation can be performed at the same time as localization, velocity distribution of blood flow can be found.

Figure 15:
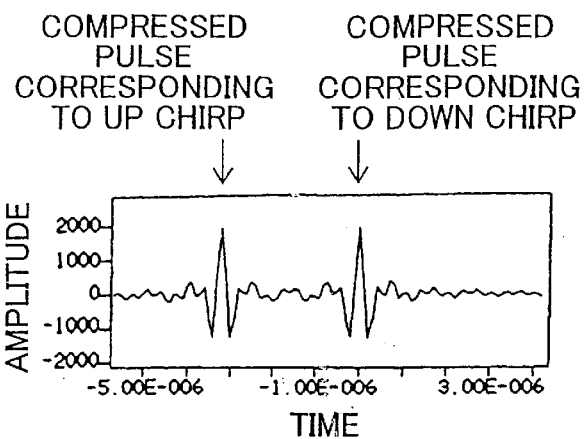
FIG. 15 is a measurement example of Doppler frequency at the temporal intervals of compressed pulses.
Figure 15:
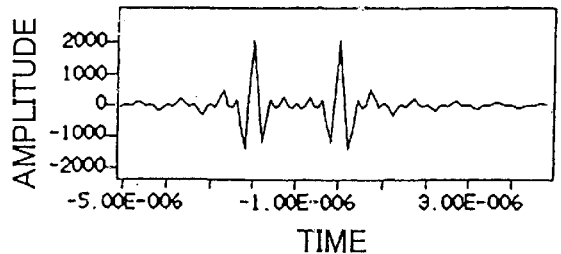
Figure 15:
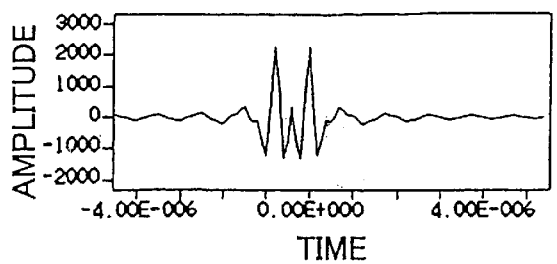

In FIG. 15 examples of Doppler frequency measurement depending on comparison of the time interval between gate circuit 1 and gate circuit 2 in FIG. 14 is shown. Here the center frequency of the transmitting chirp signal is shifted ahead of time, and using as reference the intervals at the time when there is no Doppler effect, an increase/decrease in the Doppler effect and an increase/decrease in the pulse interval are harmonized. Namely, compared to intervals without the Doppler effect shown in FIG. 15(b), if the Doppler effect is positive as shown in FIG. 15(a), the intervals between pulses widen; if the Doppler effect is negative, as shown in FIG. 15(b), the intervals between pulses narrow. By detecting this difference, the Doppler effect at the subject location can be measured.

Figure 16:
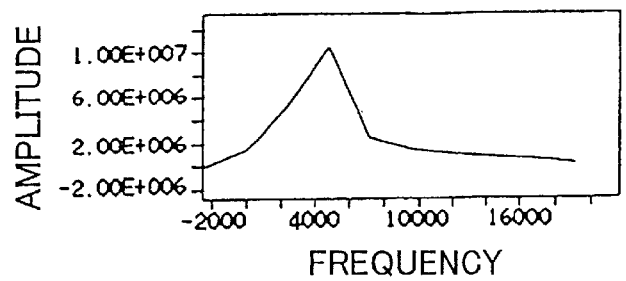
FIG. 16 is a measurement example of Doppler frequency through spectral comparison.
Figure 16:
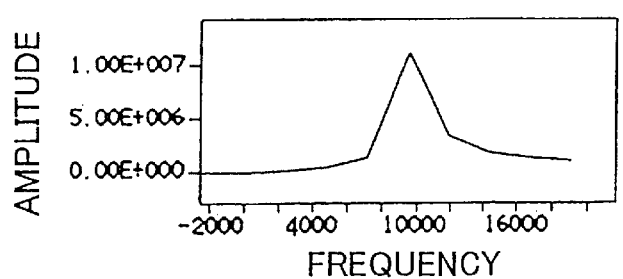
Figure 16:
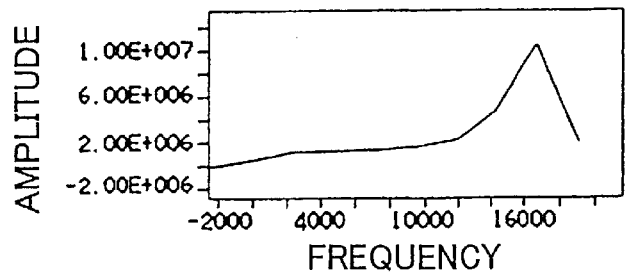

In FIG. 16, a measurement example of the Doppler frequency by spectrum analysis is shown. Here the center frequency of the transmitting chirp signal is shifted in advance, and using as a reference the intervals in the case without the Doppler effect, the increase and decrease of the Doppler effect and the shift of spectrum are corresponded. In short, when there is no Doppler effect, as shown in FIG. 16(b), the center of spectrum is assumed to be 10 khz. If the Doppler effect is positive, as shown in FIG. 16(a), the center of the spectrum shifts to the low frequency side; if the Doppler effect is negative, the center of spectrum shifts to the high frequency side. By detecting this, frequency shift due to the Doppler effect (the Doppler frequency) can be detected.

Other Intraluminal Systems

Figure 17:
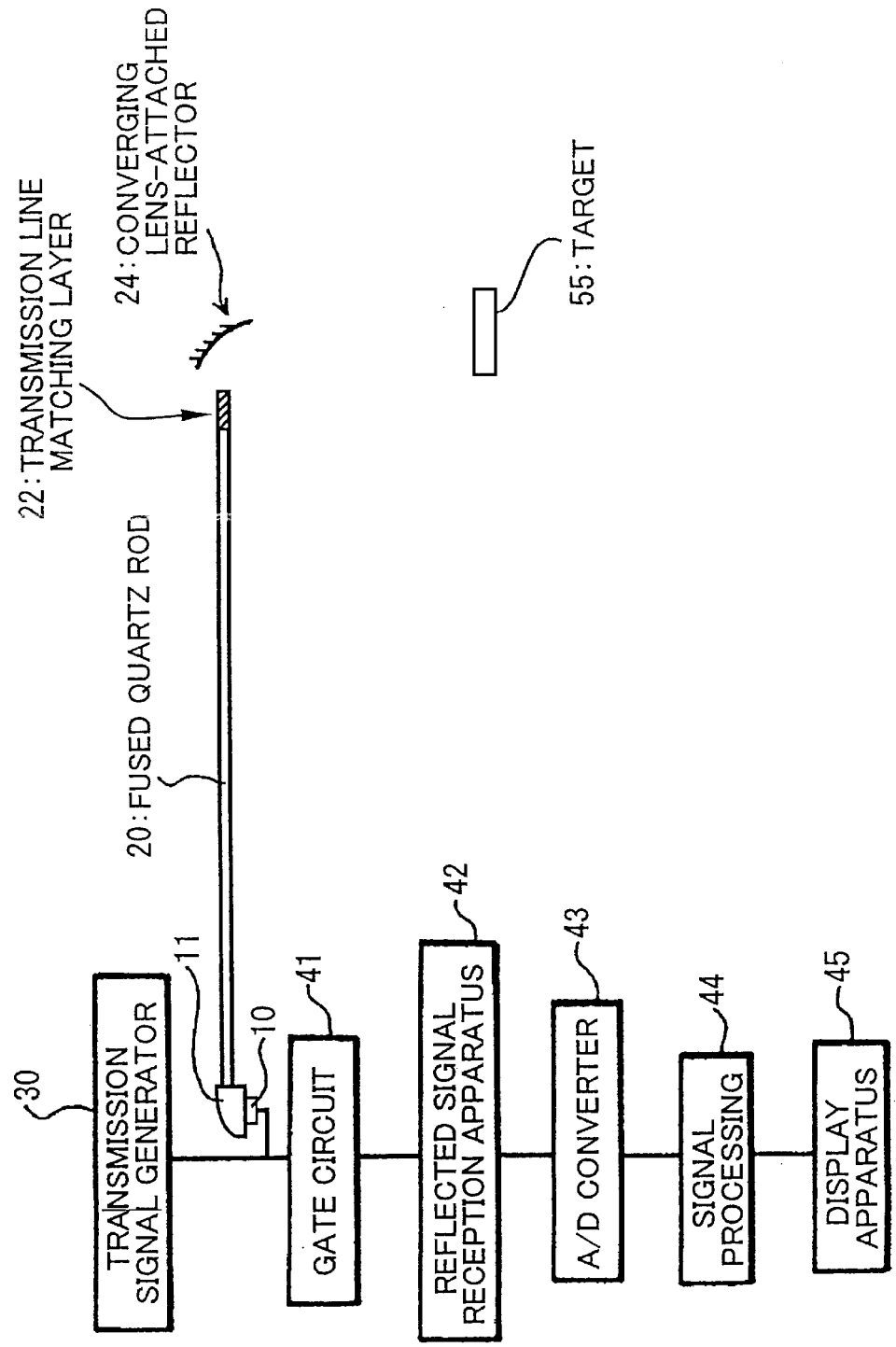
FIG. 17 is a diagram describing another configuration of the intraluminal system.

Other example of the present invention being applied to an intraluminal system is described using FIG. 17.

An ultrasound endoscope of a system where the object to be viewed is a lumen such as inside a blood vessel or inside the uterer, and where a probe mechanically rotates, is used with an ultrasound transducer 10 built into the catheter. This is the same as the system used in FIG. 7. Since it is desirable that the transmission line of this system have better flexibility, it is configured using the L(0,1) mode.

Figure 18:
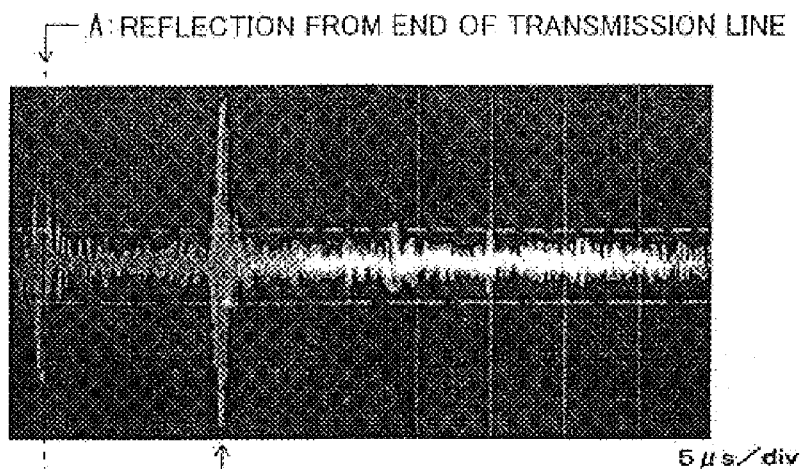
FIG. 18 is a diagram of waveform observation results from the use of the another configuration of the intraluminal system.
Figure 18:
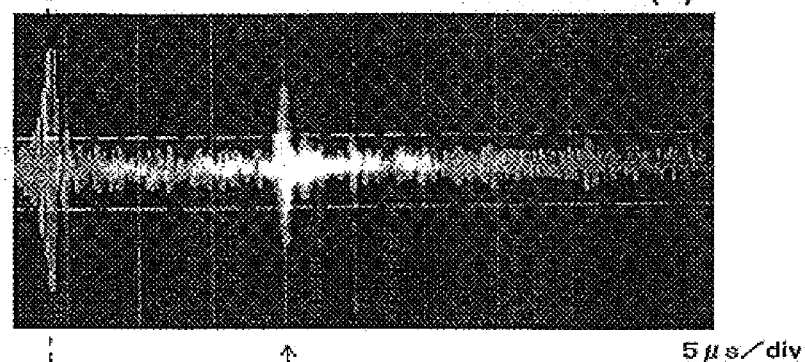
Figure 18:
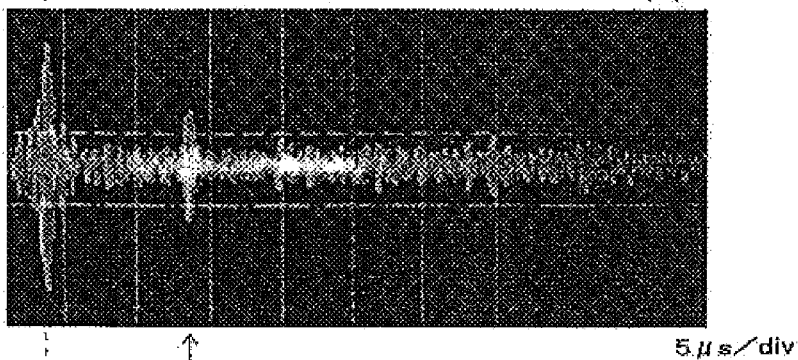

This is shown in FIG. 17. In other words, the L(0,1) mode elastic wave in the 20 Mhz band is transmitted through a quartz rod with a diameter of approximately 125 $\mu$m. In this experiment, a dielectric line (Stycast 2651 mm) with a diameter of 150 $\mu$m and a length of 37 $\mu$m is used as matching layer 22 (a matching transmission line) and is attached to the end of fused quartz rod 20 having a diameter of 125 $\mu$m and a length of 60cm. The matching layer acts as a coupler between the transmission line and water. This matching layer-attached transmission line is inserted into a metal tube and subjected to a waterproofing process. It is carefully considered that a portion of the rotating ellipsoid body be used as converging lens 24, and the edge of the transmission line is located on the focal point of the lens. In addition, in this case, since it is necessary to excite a large amplitude ultrasound wave in a narrow line, the ultrasound wave excited by transducer 10 is transmitted and received by the fused quartz rod via ultrasound paraboloid mirror 11. This lens can be set near the specimen to be measured. The ultrasound wave excited by transducer 10 irradiates target region 55 through fused quartz rod 20 and the coupler; the reflected wave then propagates in reverse through quartz rod 20 and is converted back to an electric signal by transducer 10. When the transmitted signal is set so that the received signal becomes a linear chirp signal, the received signal is converted to a compressed pulse by a standardized digital signal processing by signal processing unit 44 after passing through a standardized pulse compression filter or an A/D converter. This can be observed with displaying apparatus 45. An example of the observed waveform is shown in FIG. 18.

FIG. 18(a) is an example where a reflection from an aluminum plate in water is observed. After reflection A from the transmission end surface, reflected waveform B from the aluminum plate in water can be clearly observed. FIG. 18(b) is an example where a reflection from an acrylic plate in water is observed; and FIG. 18(c) is an example where an optical fiber having a diameter of 125 $\mu$m is observed in water. In both examples, after reflected waveform A form the transmission end surface, it is possible to observe reflected waveforms C and D from the target object.

In this system, it is possible to use a non-linear chirp signal as the transmission signal, and also to perform side lobe suppression processing using an ideal output waveform of the above-mentioned pulse compression filter as processing of the reception signal.

In addition, the above mentioned two-step compression processing can also be used.

INDUSTRIAL APPLICABILITY

With the present invention, in ultrasound transmission and reception using a chirp signal, by using a flexible waveguide transmission line as the transmission line, and by using said transmission line as a delay medium, it is possible to temporally separate a transmission signal and a reception signal with a certain extended duration. For this transmission line, a quartz rod having both ends tapered may be used.

When a transmission line is long, a chirp signal tends to be distorted; however, the use of non-linear chirp signal makes it possible to suppress distortion in the reception signal.

Furthermore, by utilizing an ideal output waveform of a pulse compressed, it is possible to perform side lobe suppression in reception signals.

By transmitting multiple chirp signals in accordance with a code line, two-step compression processing becomes possible and reception signals can be obtained having a higher signal-to-noise ratio.

Moreover, by using up chirp signals and down chirp signals, it is possible to accurately measure the Doppler effect.

What is claimed is:

1. An ultrasound transmission/reception apparatus, which performs pulse compression on a received ultrasound signal using a signal with temporally changing frequency as an ultrasound signal to be transmitted; said ultrasound transmission/reception apparatus comprising:

a transducer common for receiving and transmitting said ultrasound signal; and a transmission line common for propagating said ultrasound signal; wherein a flexible quartz is used as said transmission line, and said quartz is used as a delay medium to temporally separate a received ultrasound signal and a transmitted ultrasound signal.

2. The ultrasound transmission/reception apparatus according to claim 1, wherein a signal with a frequency that changes but not in proportion to time is used as said transmitted ultrasound signal, and said signal to be transmitted is a signal which becomes a signal with frequency that changes in proportion to time upon reception.

3. The ultrasound transmission/reception apparatus according to claim 1, wherein, side lobe suppression is performed by taking the correlation between an ideally compressed waveform that is pulse compressed and the signal obtained by pulse compressing a received ultrasound signal.

4. The ultrasound transmission/reception apparatus according to any of claim 1 through claim 3, wherein a plurality of ultrasound signals delayed a certain length of time are encoded in conformity with whether being sent according to a code series and transmitted; and after subjecting received signals to pulse compression, they are decoded in conformity with a code series that has been coded.

5. The ultrasound transmission/reception apparatus according to any of claim 1 through claim 3, wherein a tapered quartz rod with a narrowed center is used as said transmission line.

6. A Doppler measurement apparatus, which uses the ultrasound transmission/reception apparatus according to any of claim 1 through claim 3; which:

uses as a received ultrasound signal, both a signal where frequency increases with time and a signal where frequency decreases with time; and detects a Doppler signal from time difference of compressed pulses obtained by processing said respective signals received.

7. The Doppler measurement apparatus according to any of claim 1 through claim 3 which:

uses as a received ultrasound signal, a signal where frequency increases with time and a signal where frequency decreases with time; and detects a Doppler signal by performing convolution of a compressed pulse obtained through processing said respective signals received and a standard chirp signal and performing spectral analysis.

8. An interluminary ultrasound endoscope system, which uses the ultrasound transmission/reception apparatus according to any one of claim 1 through claim 3;

said interluminary ultrasound endoscope system comprising a matching layer on the specimen side end of said transmission line.

* * * * *